Aug. 18, 1964 W. E. DUFFETT Plant Pat. 2,438
CHRYSANTHEMUM PLANT
Filed Oct. 4, 1963
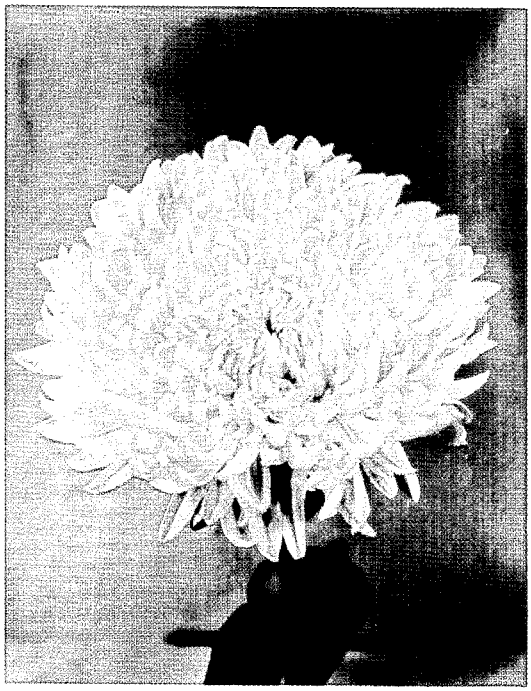
INVENTOR.
W. E. DUFFETT
BY Robb & Robb
attorneys United States Patent Office Plant Pat. 2,438
Patented Aug. 18, 1964

2,438
CHRYSANTHEMUM PLANT

William E. Duffett, Barberton, Ohio, assignor, by mesne assignments, to George J. Ball, Inc., West Chicago, Ill.

Filed Oct. 4, 1963, Ser. No. 314,083
1 Claim. (Cl. Plt.—78)

My present invention comprises a new and distinct variety of chrysanthemum plant which is a sport of the variety disclosed in U.S. Plant Patent No. 2,005.

The parent variety, U.S. Plant Patent No. 2,005, was developed as a result of a program of hybridization and cross breeding carried on in the vicinity of Niles, Michigan, said program producing a large number of chrysanthemum plants having very desirable characteristics, and when grown in production in the vicinity of Barberton, Ohio, has resulted in a number of sports, from the several parent varieties, this instant sport of my discovery being of substantial value and an improvement over the parent as well as being a substantial improvement over other known varieties of the same general hybridization and cross breeding program.

The primary difference between the instant variety and the parent variety, resides in the color thereof since the flower size, shape, form and flowering dates are very nearly the same or at least substantially so.

The novelty residing in the color largely, it is notable that the color as such is a brilliant to vivid yellow in general tonality and the blooms are described as they appear with relation to the disclosure of colors in the Nickerson Color Fan published by the Munsell Color Company. As grown in the vicinity of Barberton, Ohio, under uniform culture, plants of my new variety produce large size blooms on long strong stems, very early and continuously, the improvement of the qualities of the plant for the purposes of cut flowers being substantial.

My new variety may be compared to other varieties found during the same course of hybridization and particularly the variety of Plant Patent No. 2,274 is related thereto, and for comparison the plant of my new variety is taller and makes a more desirable cut garden chrysanthemum than the said chrysanthemum of Plant Patent No. 2,274.

Under conditions of culture previously mentioned which were undertaken in the vicinity of Barberton, Ohio, my new variety blooms from early September and substantially continuously to a killing frost. The buds of my new variety are large and are only affected by a continuous period of wet weather, and hot weather is found to delay flowering somewhat.

The blooms of my new variety are large and when fully expanded reach a diameter of approximately 6 inches, the stems being on the order of 34 inches and making a plant of that general size.

My new variety has been asexually reproduced by stem cuttings in the vicinity of Barberton, Ohio, and my new variety has been found to retain its distinctive characteristics through successive asexual reproduction.

The accompanying drawing forming a part hereof shows a typical bloom of my new variety of chrysanthemum.

The following is a detailed description of my new variety of chrysanthemum plant, the color references being to the Nickerson Color Fan published by the Munsell Color Company:

Parentage: Sport of Plant Patent No. 2,005.
Classification: Botanic—*Chrysanthemum indicum.*

*Flower*

Blooming habit: Blooms profusely from early September until a killing frost and continuously. Observations were made in the vicinity of Barberton, Ohio, in September.

Bud:
- *Size.*—Large.
- *Form.*—Globular. Affected by rot in wet weather and hot weather delays flowering.
- *Color.*—When sepals first divide—between 5Y 8/12 Vivid Yellow and 2.5Y 8/12 Vivid Yellow. When petals begin to unfurl—between 7.5Y 9/8 Brilliant Greenish Yellow and 7.5Y 8/12 Vivid Greenish Yellow. When half blown: inside of petals—between 7.5Y 9/8 Brilliant Greenish Yellow and 5Y 9/9 Brilliant Yellow; reverse of petals—7.5Y 9/8 Brilliant Greenish Yellow.
- *Sepals.*—Smooth edge.
- *Calyx.*—Shape — apple. Size — broad. Aspect—heavy.
- *Peduncle.* — Length — medium. Aspect — smooth. Strength—stiff and erect. Bud opens well and hot weather delays flowering.

Bloom:
- *Size.*—Large. Average size when fully expanded—6".
- *Borne.*—Clusters and rounded.
- *Stems.*—Long and strong.
- *Form.*—When first open—globular. Permanence—retains its form to the end.
- *Petalage.*—Very double with too many petals to count under normal conditions.
- *Color.*—Center of flower—between 5Y 8/12 Vivid Yellow and 2.5Y 8/12 Vivid Yellow. Outer petals—between 7.5Y 9/8 Brilliant Greenish Yellow and 7.5Y 8/12 Vivid Greenish Yellow. Base of Petals (singlet)—5Y 9/9 Brilliant Yellow. Inside of petals—between 7.5Y 9/8 Brilliant Greenish Yellow and 5Y 9/9 Brilliant Yellow. Reverse of petals—somewhat lighter than 7.5Y 9/8 Brilliant Greenish Yellow. General tonality from a distance—between 2.5Y 9/9 Brilliant Yellow and 2.5Y 8/12 Vivid Yellow.
- *Discoloration.*—General tonality at end of: First week—between 2.5Y 9/9 Brilliant Yellow and 5Y 8/12 Vivid Yellow. Second week—between 5Y 9/9 Brilliant Yellow and 2.5Y 9/9 Brilliant Yellow. Third week—7.5Y 9/8 Brilliant Greenish Yellow.

Petals:
- *Texture.*—Thick and leathery.
- *Appearance.*—Inside—satiny. Outside—shiny.
- *Form.*—Oval.
- *Arrangement.*—Irregular.
- *Persistence.*—Hang on and dry.
- *Fragrance.*—None.
- *Lastingness.*—On the plant—long. As cut flower—long.

Genital organs:

*Stamens, anthers.*—Small and many.

*Arrangement.*—Mixed with petaloids.

*Stamens, filaments.*—Medium.

*Styles.*—Bunched and of medium length.

Plant:

*Form.*—Bush.

*Growth.*—Vigorous.

*Height.*—34 inches.

Foliage:

*Size.*—Large.

*Quantity*—Normal.

*Shape.*—Oval indented.

*Texture.*—Glossy.

*Edge.*—Smooth.

*Stipules.*—Short and smooth. Somewhat susceptible to mildew.

I claim:

A new and distinct variety of chrysanthemum plant substantially as herein disclosed, characterized as to novelty by the brilliant to vivid yellow color of its blooms, tall growth habit with blooms on long, strong stems, very early, continuous and long blooming period, the large size of its blooms, and its improved qualities as a cut flower.

No references cited.